US006284943B1

(12) United States Patent
Osborn, III et al.

(10) Patent No.: US 6,284,943 B1
(45) Date of Patent: Sep. 4, 2001

(54) ABSORBENT ARTICLE HAVING INCREASED FLEXIBILITY IN USE

(75) Inventors: Thomas Ward Osborn, III; Letha Margie Hines, both of Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 08/766,564

(22) Filed: Dec. 13, 1996

(51) Int. Cl.$^7$ .................................................... A61F 13/15
(52) U.S. Cl. .......................... 604/366; 604/370; 604/372; 604/374; 604/385.01; 604/385.04; 604/385.31; 604/387
(58) Field of Search ............................ 604/297, 364–366, 604/378–382, 385.1, 387, 359, 360, 374, 368, 369, 385.07, 385.36, 370, 372, 375

(56) References Cited

U.S. PATENT DOCUMENTS

| 810,117 | * | 1/1906 | Green ..................................... 604/378 |
| 2,067,961 | * | 1/1937 | Williams ................................ 604/378 |
| 3,070,095 | * | 12/1962 | Torr ....................................... 604/368 |
| 3,444,859 | * | 5/1969 | Kalwaites ............................... 604/369 |
| 3,570,493 | | 3/1971 | Olsson . |
| 3,717,150 | | 2/1973 | Schwartz . |
| 4,103,062 | | 7/1978 | Aberson et al. . |
| 4,195,634 | | 4/1980 | DiSalvo et al. . |
| 4,217,901 | | 8/1980 | Bradstreet et al. . |
| 4,232,674 | | 11/1980 | Melican . |
| 4,605,402 | | 8/1986 | Iskra . |
| 4,710,187 | | 12/1987 | Boland et al. . |
| 4,752,349 | | 6/1988 | Gebel . |
| 4,773,905 | * | 9/1988 | Molee et al. .......................... 604/378 |
| 4,865,597 | | 9/1989 | Mason, Jr. et al. . |
| 4,936,839 | * | 6/1990 | Molee et al. .......................... 604/378 |
| 4,950,264 | | 8/1990 | Osborn, III . |
| 4,992,324 | | 2/1991 | Dube . |
| 5,009,653 | | 4/1991 | Osborn, III . |
| 5,098,422 | | 3/1992 | Davis et al. . |
| 5,171,302 | | 12/1992 | Buell . |
| 5,248,309 | | 9/1993 | Serbiak et al. . |
| 5,295,988 | | 3/1994 | Muckenfuhs et al. . |
| 5,300,055 | | 4/1994 | Buell . |
| 5,324,278 | | 6/1994 | Visscher et al. . |
| 5,374,260 | | 12/1994 | Lemay et al. . |
| 5,382,467 | | 1/1995 | Widlund et al. . |
| 5,429,633 | | 7/1995 | Davis et al. . |
| 5,460,623 | | 10/1995 | Emenaker et al. . |
| 5,490,847 | | 2/1996 | Correa et al. . |
| 5,518,801 | | 5/1996 | Chappell et al. . |

FOREIGN PATENT DOCUMENTS

| 0 467 409 A1 | 1/1992 | (EP) . |
| 2 168 612 A | 6/1986 | (GB) . |
| 2 191 098 A | 12/1987 | (GB) . |
| WO 91/00720 | 1/1991 | (WO) . |
| WO 94/16658 | 8/1994 | (WO) . |

* cited by examiner

Primary Examiner—John G. Weiss
Assistant Examiner—K. M. Reichle
(74) Attorney, Agent, or Firm—Matthew P Fitzpatrick; Jeffrey V Bamber

(57) ABSTRACT

A disposable absorbent article for wearing in an undergarment, such as a sanitary napkin, pantiliner, or incontinence pad is described. The absorbent article includes a topsheet, a backsheet, an absorbent core, and a stiffening feature. The stiffening feature places the absorbent article in an initially stiffened condition during placement of the article in an undergarment. After the article is subjected to the forces exerted by the body of the wearer, the stiffening feature no longer provides an increased initial stiffness and the article becomes more flexible.

23 Claims, 9 Drawing Sheets

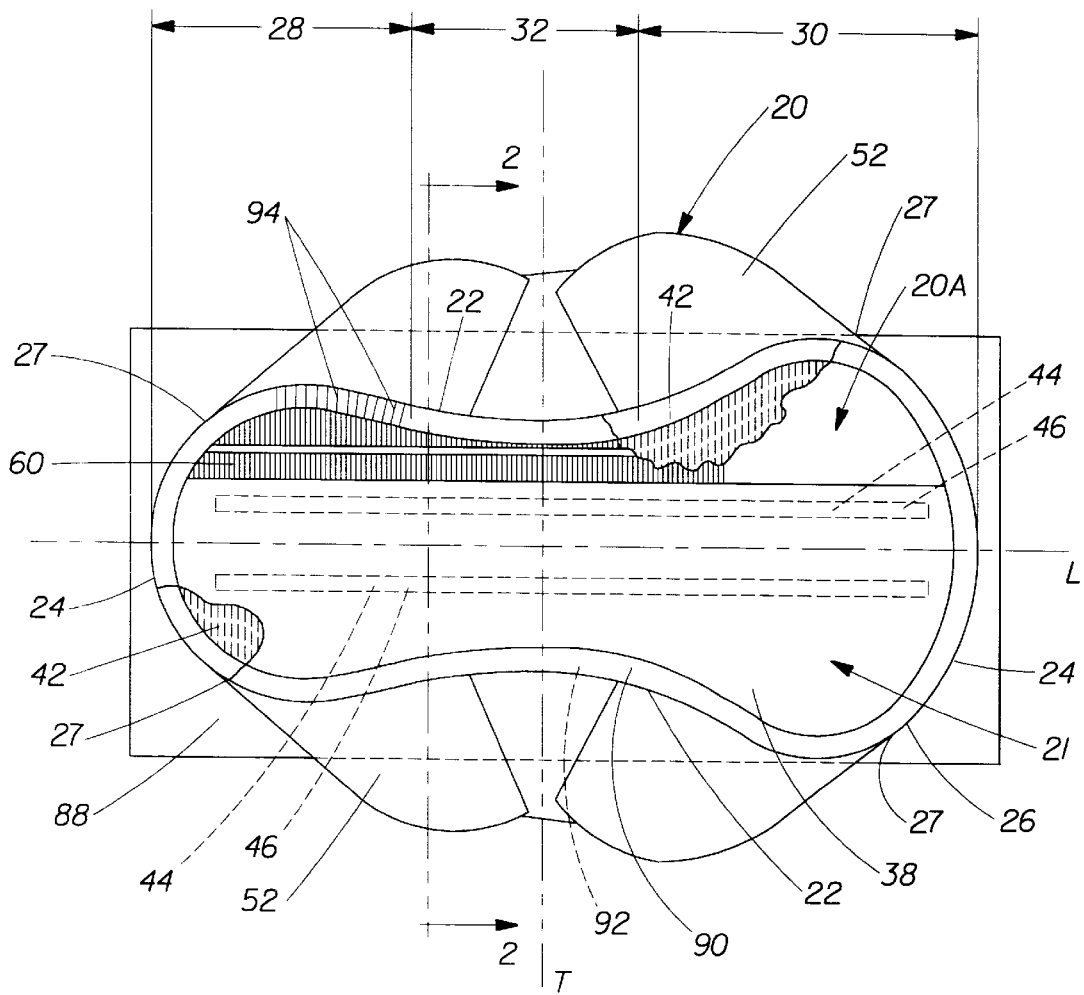
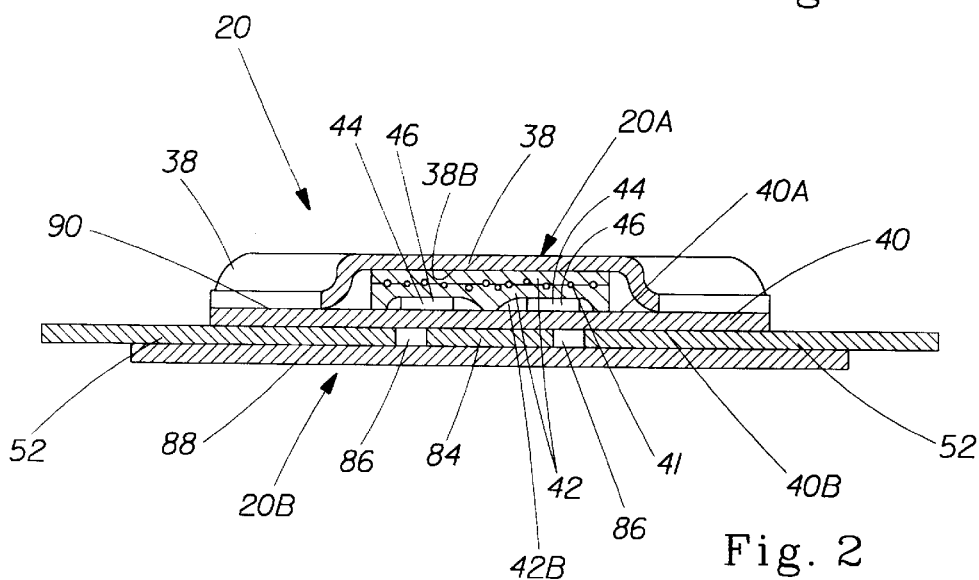
Fig. 1
Fig. 2

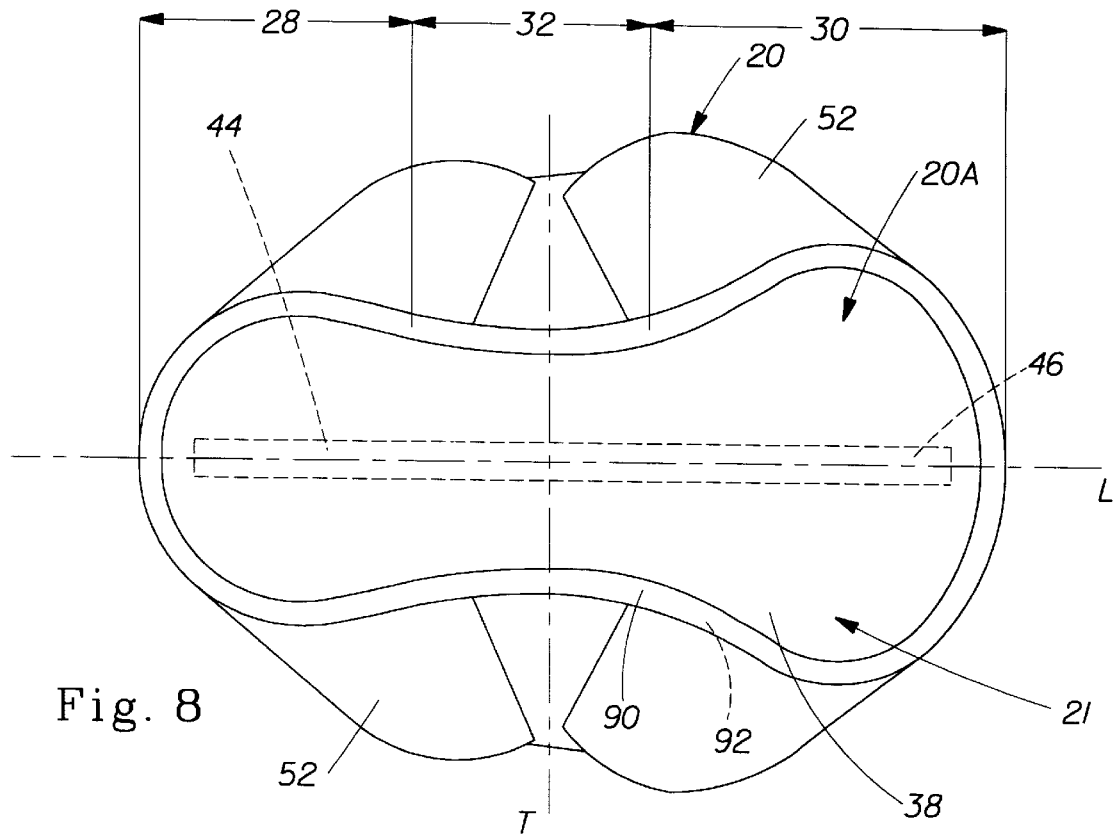
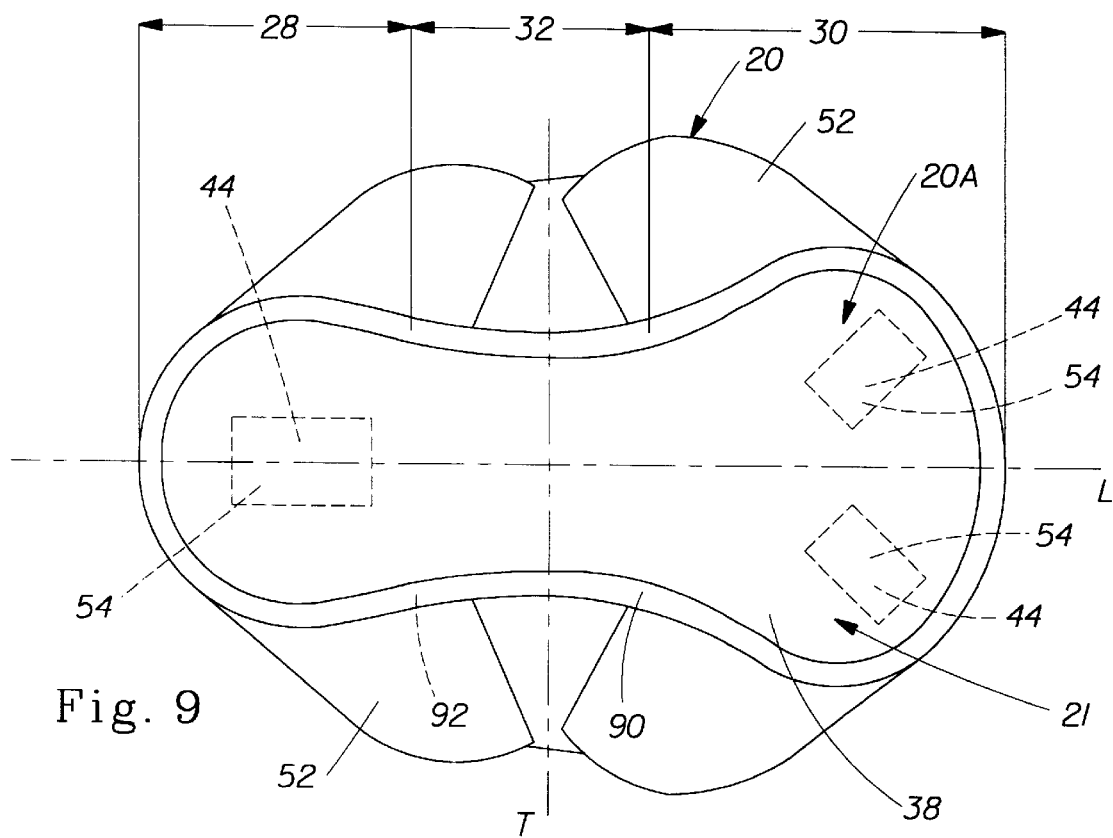

ABSORBENT ARTICLE HAVING INCREASED FLEXIBILITY IN USE

FIELD OF INVENTION

The present invention relates generally to absorbent articles such as sanitary napkins, pantiliners, and incontinence pads. More particularly, the present invention relates to sanitary napkins which are relatively stiff during placement of the sanitary napkin in an undergarment and as the undergarment is pulled into position, but which exhibit high levels of flexibility and drape during wear.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineal area of the body.

It has been found desirable to construct absorbent articles which are thin, extensible, soft, and highly drapable. Such an extensible, flexible absorbent article is disclosed in PCT Application Publication No. 95/20931, published Aug. 10, 1995. These high levels of flexibility and drape provide comfortable products with low wearing awareness. To more effectively handle such articles, however, higher stiffness and rigidity are often required to prevent the end of the article from folding over as the article is placed into the undergarment and as the undergarment is pulled into position. The apparent contradiction of providing an absorbent article which is both flexible and stiff can be overcome by recognizing that the needs for stiffness and flexibility are not required simultaneously, but are needs which are separated in time.

Many current absorbent articles, particularly those with airfelt absorbent cores are soft and flexible when first placed in an undergarment, but become more stiff when wet. Such flexible-then stiff characteristics are seen in absorbent articles with other types of cores as well. U.S. Pat. No. 5,374,260 issued to Lemay, et al. on Dec. 20, 1994 discloses a sanitary napkin with a peat moss core which is flexible, then more stiff when moisture is absorbed. It is also known in the art to apply resilient structures to absorbent articles to impart an overall resiliency to the article or portions of the article. U.S. Pat. No. 5,098,422 issued to Davis, et al. on Mar. 24, 1992 describes such a form-retaining sanitary napkin. This form retaining resiliency, however, remains throughout the life of the sanitary napkin.

A need, therefore, exists for a disposable absorbent article which is relatively stiff when handled and applied to an undergarment, but which becomes more flexible when worn. Such an absorbent article has the advantage of being easy to handle and apply to an undergarment without the article folding over or adhering to itself while also offering the greatest comfort and low wearing awareness during subsequent wear. It is therefore an object of the present invention to provide an absorbent article, such as a sanitary napkin, which is relatively stiff when handled and applied to an undergarment but which becomes more flexible when worn.

This and other objects of the present invention will be more readily apparent when considered in reference to the following description and when taken in conjunction with the accompanying drawings.

SUMMARY OF THE INVENTION

The present invention provides an absorbent article, such as a sanitary napkin, pantiliner, or incontinence pad. More particularly, the present invention is directed to a sanitary napkin which is generally stiff when handled and applied to an undergarment, but which becomes more flexible when worn.

The sanitary napkin comprises a liquid pervious topsheet, a liquid impervious backsheet joined to the topsheet, and an absorbent core positioned between the topsheet and the backsheet. The sanitary napkin is also provided with a stiffening feature which imparts an initial stiffness to the sanitary napkin. The stiffening feature may comprise one or more stiffening members or the stiffening feature may be provided directly by the structure of one or more of the previously named elements (i.e., the topsheet, the backsheet, and the absorbent core).

The stiffening feature of the present invention provides the sanitary napkin with a degree of stiffness when it is handled and applied to an undergarment, but not when the napkin is worn. The sanitary napkin is preferably generally flexible when worn. In a particularly preferred embodiment, the sanitary napkin is also very thin, extensible, soft, and highly drapable when worn so that it is more cloth-like and less plastic like (like many current sanitary napkins). The main body portion of this preferred napkin extends with the wearer's undergarments and provides sustained coverage of a large portion of the wearer's panties.

In a preferred embodiment, the difference in stiffness between handling the sanitary napkin and wearing the sanitary napkin is accomplished through the use of brittle strips of material which shatter when subjected to the normal forces associated with wearing of the article (e.g. from wearer sitting or walking). These strips are preferably located between the backsheet and absorbent core.

In an alternate preferred embodiment the stiffening feature may comprise a tube shaped member constructed of a tissue layer wrapped in a polypropylene layer. The polypropylene layer is preferably melted into the tissue layer to provide the requisite initial stiffness. The tube structure collapses when the wearer sits down, thereby allowing the sanitary napkin to assume a generally flexible state.

In yet an additional preferred embodiment, the stiffening feature comprises zones of stiffness which occupy at least a portion of the sanitary napkin. The zones of stiffness may be stiffened locations on the topsheet, the backsheet, the core or some combination of these. The zones of stiffness may comprise a stiffened layer of material such as a tissue layer stiffened by melting a polypropylene layer into it. This stiffened layer is then bonded to the backsheet, topsheet, or absorbent core of the sanitary napkin. The increased stiffness provided by the zones of stiffness is lost once the sanitary napkin is subjected to the normal forces of wear, thereby allowing the sanitary napkin to assume a generally flexible state.

The sanitary napkin, can, and preferably does, also comprise various additional components and/or features. For example, the sanitary napkin preferably comprises a pair of side extensions that extend laterally outward from the main body portion of the napkin.

BRIEF DESCRIPTION OF THE DRAWINGS

While the Specification concludes with claims particularly pointing out and distinctly claiming the present invention, the invention will be better understood from the following description taken in conjunction with the accompanying drawings in which like designations are used to designate substantially identical elements, and in which:

FIG. 1 is a top plan view of a preferred embodiment of the sanitary napkin present invention showing a partial cutaway of the topsheet to reveal the underlying core structure.

FIG. 2 is a sectional view taken along line 2—2 of the sanitary napkin shown in FIG. 1.

FIG. 8 is a simplified top plan view of an additional preferred embodiment of he sanitary napkin of the present invention.

FIG. 9 is a simplified top plan view of an additional embodiment of the sanitary napkin of the present invention.

DETAILED DESCRIPTION OF THE INVENTION

The present invention relates to absorbent articles which have an initially stiffened condition during placement of the article in an undergarment and as the undergarment is pulled into position, but which are more flexible during wear.

The term "absorbent article," as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinence pads (and other articles worn in the crotch region of a garment). The term "disposable" refers to articles which are intended to be discarded after a single use and preferably recycled, composted, or otherwise disposed of in an environmentally compatible manner. That is, they are not intended to be laundered or otherwise restored or reused as an absorbent article.

Figure 3:
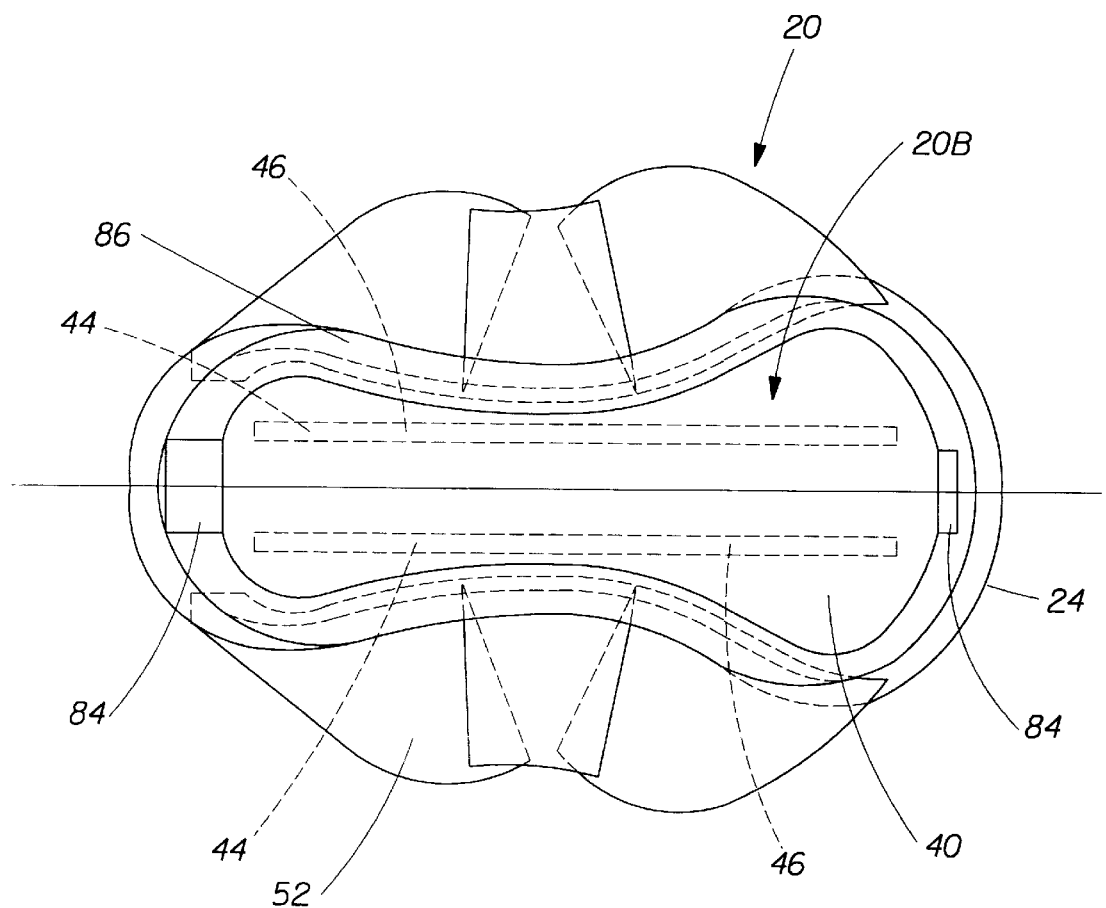
FIG. 3 is a bottom plan view of the sanitary napkin shown in FIG. 1 with the release paper removed from the adhesive on the backsheet.

FIGS. 1–3 show a preferred embodiment of a disposable absorbent article of the present invention. In the preferred embodiment illustrated, the absorbent article is a sanitary napkin designated 20.

The term "sanitary napkin," as used herein, refers to an article which is worn by females adjacent to the pudendal region that is intended to absorb and contain the various exudates which are discharged from the body (e.g., blood, menses, and urine). It should be understood, however, that the present invention is also applicable to other feminine hygiene or catamenial pads such as panty liners, or other absorbent articles such as incontinence pads, and the like.

The sanitary napkin has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a principal longitudinal centerline L and a principal transverse centerline T. The term "longitudinal," as used herein, refers to a line, axis, or direction in the plane of the sanitary napkin 20 that is generally aligned with (i.e. approximately parallel to) a vertical plane which bisects a standing wearer into left and right body halves when the sanitary napkin 20 is worn. The terms "transverse" or "lateral," used herein, are interchangeable and refer to a line, axis, or direction generally perpendicular to the longitudinal direction. The sanitary napkin 20 has a longitudinal dimension that runs in the general direction of the principal longitudinal centerline L, and a (typically shorter) transverse dimension that runs in the general direction of the principal transverse centerline T.

FIG. 1 shows that the sanitary napkin 20 has a main body portion 21 with two spaced apart longitudinal edges 22, two spaced apart transverse or end edges (or "ends") 24, and four corners 27, which together form the periphery 26 of the main body portion 21 of the sanitary napkin 20. The main body portion 21 also has two end regions, which are designated first end region 28 and second end region 30. A central region 32 is disposed between the end regions 28 and 30. The end regions 28 and 30 extend outwardly from the edges of the central region 32 about ⅛ to ⅓ of the length of the main body portion. A detailed description of a central region and two end regions for a sanitary napkin is contained in U.S. Pat. No. 4,690,680 issued to Higgins on Sep. 1, 1987.

The sanitary napkin 20 (or main body portion thereof) can be of any thickness, including relatively thick, intermediate thickness, relatively thin, or even very thin. The embodiment of the sanitary napkin 20 shown in FIGS. 1–3 of the drawings is intended to be an example of a relatively thin sanitary napkin (having a caliper of less than or equal to about 5 mm, more preferably less than or equal to about 4 mm), and preferably is an "ultra-thin" sanitary napkin. It should be understood, however, when viewing these figures the number of layers of material shown causes the sanitary napkin 20 to appear much thicker than it actually is. An "ultra-thin" sanitary napkin 20 as described in U.S. Pat. Nos. 4,950,264 and 5,009,653 issued to Osborn preferably has a caliper of less than about 3 millimeters. The thin sanitary napkin 20 shown should also be preferably relatively flexible, so that it is comfortable for the wearer.

FIG. 2 shows the individual components of the sanitary napkin 20 of the present invention. The sanitary napkin shown in FIG. 2 generally comprises at least a liquid pervious topsheet 38, a liquid impervious backsheet 40, and an absorbent core 42. The sanitary napkin 20 is also provided with at least one stiffening feature 44. In the preferred embodiment shown in FIG. 2, the stiffening feature 44 comprises a pair of brittle strip stiffening members 46. The absorbent core 42 and preferably the brittle strip stiffening members 46 are positioned between the topsheet 38 and the backsheet 40. More preferably, the brittle strips 46 are positioned between the backsheet 40 and the absorbent core 42 or within the absorbent core 42, but the brittle strips 46 may also be positioned between the topsheet 38 and the absorbent core 42, or, less preferably, on the garment facing side of the backsheet 40B.

The components of the sanitary napkin 20 may comprise suitable materials described in the patents incorporated by reference herein. The sanitary napkin 20 may, but need not, be comprised of extensible components. Preferably, however, the sanitary napkin 20 is comprised of one or more extensible components, and more preferably, is comprised of all extensible components and thus, has an overall extensibility during wear. Suitable extensible materials for the components of the sanitary napkin 20 are described in U.S. patent application Ser. No. 07/915,133 filed Jul. 23, 1992, in the name of Osborn , et al. (PCT Publication No. WO 93/01785 published Feb. 4, 1993), now pending in the form of allowed continuation application Ser. No. 08/503,895 filed on Jul. 18, 1995; U.S. patent application Ser. No. 07/915,284 filed Jul. 23, 1992, in the name of Osborn, et al. (PCT Publication No. 93/01786 published Feb. 4, 1993), now pending in the form of allowed divisional application Ser. Nos. 08/472,156 and 08/476,238 both filed on Jun. 7, 1995; and U.S. patent application Ser. No. 08/192,240 filed Feb. 4, 1994 in the name of Osborn, et al. (PCT Publication No. WO 95/20931). The stiffening feature(s) 44 also may, but need not, be extensible. The extensibility characteristics of a preferred sanitary napkin 20 will now be discussed in greater detail.

Figure 4:
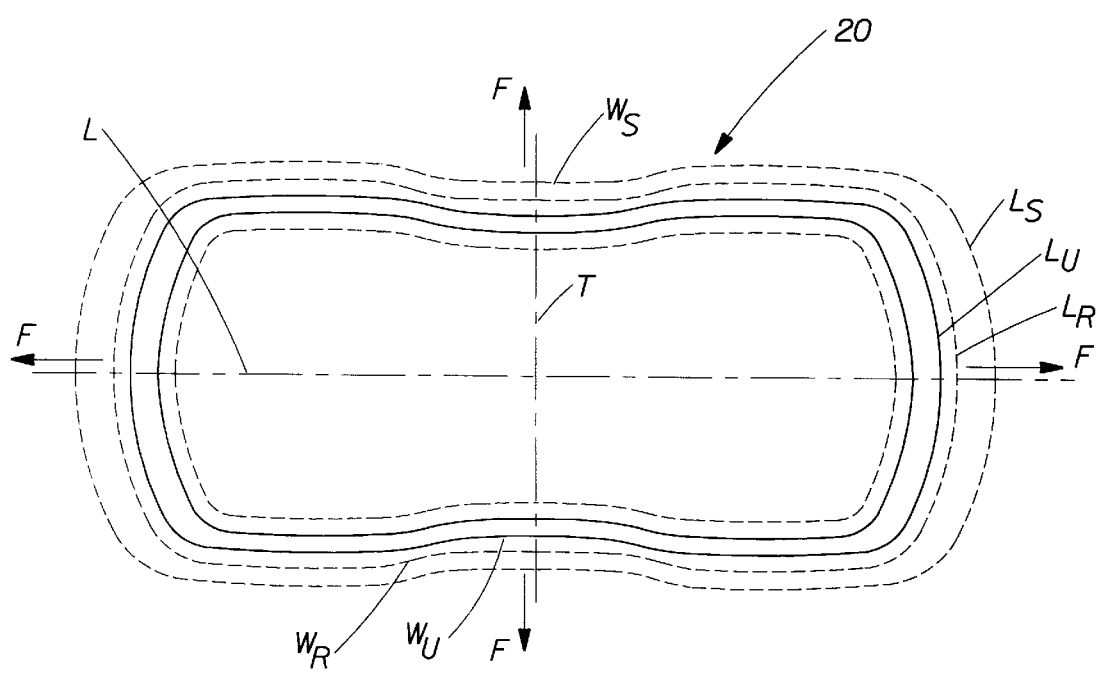
FIG. 4 is a simplified plan view showing extensibility of a sanitary napkin of a more conventional shape which has extensible components.

The extensibility of the sanitary napkin 20 is shown in a simplified fashion in FIG. 4. The term "extensible," as used herein refers to articles that can increase in at least one of their dimensions in the x-y plane. The x-y plane is a plane generally parallel to the faces of the sanitary napkin 20. The term "extensible" includes articles that are stretchable and elastically stretchable (defined below). The sanitary napkin 20 shown in FIGS. 1–3 is preferably extensible during wear both in length and width. In its most preferred embodiments, the sanitary napkin is extensible in all directions in the x-y plane. The sanitary napkin 20, in other embodiments, however, may be generally inextensible, only extensible in one of these directions, or extensible in some direction between the longitudinal and transverse directions. Preferably, the sanitary napkin 20 is extensible at least in the longitudinal direction.

The sanitary napkin 20 may in some preferred embodiments, in addition to being extensible, also be stretchable. The term "stretchable," as used herein, refers to articles that are extensible when stretching forces are applied to the article and offer some resistance to stretching. More preferably still, the sanitary napkin 20 may be elastically stretchable. The terms "elastically stretchable" and "elastically extensible" are intended to be synonymous. These terms, as used herein, mean that when the stretching forces are removed, the sanitary napkin will tend to return toward its unextended or unstretched (or "original" dimensions). The sanitary napkin 20 need not return all the way to its unstretched dimensions, however. It may, as shown in FIG. 4 return to relaxed dimensions (such as $L_R$ and $W_R$) between its unstretched dimensions (such as $L_U$ and $W_U$) and extended (or stretched) dimensions $L_S$ and $W_S$. Making the sanitary napkin elastically stretchable during wear will reduce the undesirable tendency of the sanitary napkin to gather longitudinally inward (i.e., bunch longitudinally and become sloppy) in the wearer's panties when forces which tend to stretch the sanitary napkin are removed such as when the wearer's panties contract.

The preferred sanitary napkin 20 embodiment shown in FIGS. 1–3 is preferably extensible during wear in the amounts described in previously discussed U.S. patent application Ser. No. 07/915,133, (PCT Publication No. WO 93/01785), U.S. patent application Ser. No. 07/915,284 (PCT Publications No. WO 93/01786), and U.S. patent application Ser. No. 08/192,240 (PCT Publication No. WO 95/20931). To summarize the same, the sanitary napkin 20 is preferably capable of extending about 5% to less than about 50%, more preferably between about 10% and about 40% under the forces associated with wearing the sanitary napkin in a pair of panties. Preferably, the sanitary napkin is capable of such extension under forces of between about 50 to 100 grams to about 1,000–1,500 grams, more preferably under forces of between about 250 grams and about 800 grams. The sanitary napkin 20 of the present invention can also be provided with any other features of the sanitary napkins described in the above publications including, a structure that provides a "force wall" to prevent elongation past a certain amount without substantial increases in the amount of force applied to the sanitary napkin.

In addition, in some especially preferred embodiments described in greater detail herein, various components of the sanitary napkin 20 are capable of smaller amounts of extension under forces at the low end of the broadest range set forth above (e.g., forces in the range of about 100–200 grams). For instance, in such embodiments, the sanitary napkin 20 is preferably capable of extending about 2.5%, more preferably about 3% at 100 grams of force, and about 5%, more preferably about 7.5% at 200 grams force. In absorbent articles with small amounts of extensibility under low forces, the force wall may also occur at low elongations, such as about 5% elongation, but may occur at elongations up to about 50% elongation.

Further, in embodiments of the sanitary napkin (or other absorbent article) of the present invention which are extensible, the sanitary napkin 20 is preferably extensible in at least the same amounts and under the same forces as the wearer's panties (or other undergarments) so that the panties control the extensibility of the sanitary napkin during wear. In other words, the sanitary napkin preferably has a modulus of elasticity that is close to, and preferably less than or equal to that of the undergarment in which it is placed. For example, if the undergarment requires a force to extend about 5% (or about 10%), the sanitary napkin (that is, the main body portion thereof) preferably requires a force to extend the same amount that is less than or equal to about 1.2 times, more preferably less than or equal to about 1 times the force required to extend the undergarment. The force required to extend the crotch region of a typical North American-type woman's panty in the transverse direction (at the narrowest point of the same) is about 135 g/cm. The force required to extend the portions of the back panel of such a panty where the second end region of the sanitary napkin might lie in the longitudinal direction is about 165 g/cm. A typical force to elongate the panty elastics of a North American cotton panty is about 135 g/cm. Elastic forces for other types of panties or undergarments may be somewhat higher.

The sanitary napkin 20 (or other absorbent article) of the present invention may, but need not exhibit the extensibility described above prior to the time said sanitary napkin is in place in the wearer's undergarment adjacent to the pudendal region of the body of the wearer. While the sanitary napkin is being placed in an undergarment and preferably as the undergarment holding the sanitary napkin is being pulled into position as well, the sanitary napkin displays a greater stiffness that it does during wear by virtue of the inclusion of the stiffening feature(s) 44. The stiffening feature(s) 44 imparts a temporary rigidity to the sanitary napkin 20 which inhibits its flexibility and may, if desired for ease of handling, also inhibit its extensibility prior to wear.

The absorbent article of the present invention will remain in its initially stiffened condition and may remain substantially inextensible and non-stretchable until first subjected to forces exceeding a pre-determined "initial stiffness threshold." The initial stiffness threshold may vary for different embodiments of the present invention. In all embodiments the initial stiffness threshold should be chosen to be greater than the range of forces expected to be exerted on the absorbent article during packaging, shipment, handling, and placement in an undergarment. Likewise, the force levels represented by the initial stiffiess threshold should be lower than those forces typically exerted on the absorbent article by the body of the user (e.g. from sitting, walking, etc.) once the article is in place in an undergarment. Ideally, the initial stiffness threshold should not be exceeded until the absorbent article is in place adjacent the body of the user, but should be exceeded in the earliest stages of wear (e.g., after the first few steps of the user, when the user first sits down, etc.). The appropriate initial stiffness threshold for various embodiments of the present invention is selected with these objectives in mind.

It is not necessary for the stiffening feature(s) 44 of the present invention to impart this temporary initial rigidity to the entire sanitary napkin. The objects of the invention may be achieved by imparting an initial stiffness to only a portion or portions of the absorbent article.

It is also acceptable for the initial stiffness threshold to be exceeded in localized portions of the article during packaging. For example, a sanitary napkin of the present invention may be folded in half or tri-folded during packaging along predetermined fold lines. In such a scenario the initial stiffness threshold of the sanitary napkin as described above may be exceeded along these fold lines. An absorbent article of the present invention intended to be folded during packaging may be constructed with a stiffening feature which, prior to folding, acts upon portions of the article which cross these fold lines. In such a scenario, the stiffening feature may cease to provide an increased initial stiffness in the localized area of folding when the article is folded during packaging. Alternatively, the article may be constructed with two or more independent areas of initial stiffness not crossing the fold lines thereby allowing the article to be folded without exceeding the initial stiffness threshold in any of the areas imparted with the described initial stiffness.

The preferred sanitary napkin 20 embodiment may have an initial stiffness which exceeds that of the sanitary napkin described in U.S. Pat. No. 5,460,623 issued to Emenaker, et al. on Oct. 24, 1995. Once the sanitary napkin 20 (or other absorbent article) is in place and the body of the user has exerted forces greater than the initial stiffness threshold upon the napkin, the stiffening feature(s) 44 will substantially cease to provide any increased stiffness or rigidity to the napkin. That is, even when subsequently exposed to forces below the initial stiffness threshold (after initial exposure in the early stages of wear), the sanitary napkin 20 will be respond in a manner characteristic of a generally flexible and preferably extensible and stretchable absorbent article described above. The flexibility exhibited by the sanitary napkin 20 after the initial stiffness threshold has been exceeded may approach that of the sanitary napkin described in U.S. patent application Ser. No. 08/192,240 filed Feb. 4, 1994 in the name of Osborn, et al. (PCT Publication No. WO 95/20931).

The individual components which may be suitable for the various embodiments of the sanitary napkin 20 of the present invention will now be looked at in greater detail with reference to FIGS. 1–3.

The topsheet 38 comprises a first liquid pervious component. When the sanitary napkin 20 is in use, the topsheet 38 is in close proximity to the skin of the user. The topsheet 38 may be extensible or inextensible depending on the type of absorbent article it is used with. The topsheet 38 used in the embodiment shown in FIGS. 1–3 is preferably extensible, more preferably elastically extensible, and is as compliant, soft feeling, and non-irritating to the user's skin as possible. The topsheet 38 should further exhibit good strikethrough and a reduced tendency to rewet permitting bodily discharges to rapidly penetrate it and flow toward the core 42, but not allowing such discharges to flow back through the topsheet 38 to the skin of the wearer.

A suitable topsheet 38 may be manufactured from a wide range of materials including, but not limited to woven and nonwoven materials, apertured formed thermoplastic films, apertured plastic films, and thermoplastic scrims. Suitable woven and nonwoven materials can be comprised of natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. When the topsheet 38 comprises a nonwoven web, the web may be spunbonded, carded, wet-laid, meltblown, hydrogentangled, combinations of the above, or the like.

Apertured films are generally preferred for the topsheet 38 because they are pervious to liquids and, if properly apertured, have a reduced tendency to allow liquids to pass back through and rewet the wearer's skin. Suitable apertured films are described in U.S. Pat. No. 3,929,135 issued to Thompson on Dec. 30, 1975; U.S. Pat. No. 4,324,426 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. A particularly suitable topsheet 38 is made in accordance with U.S. Pat. No. 4,342,314 issued to Radel, et al. and U.S. Pat. No. 4,463,045 issued to Ahr, et al. A topsheet 38 made of model X-3265 or model P1552 apertured formed film sold by Tredegar Corporation of Terre Haute, Indiana has been found to work well.

The topsheet 38 can be made extensible by performing a mechanical operation, such as pleating, corrugating, or ring rolling on the topsheet material to provide folds in the topsheet 38 that are able to open when the topsheet 38 is stretched. The term "ring rolling," as used herein, refers to a process of feeding the topsheet material between a pair of internally corrugated rolls. Such processes can be performed on many of the topsheet materials described above. In one preferred embodiment of the present invention, the topsheet 38 is made in accordance with U.S. Pat. No. 4,463,045 and ring rolled to provide it with a degree of longitudinal extensibility. Such a topsheet is described in U.S. Pat. No. 5,366,782 issued to Curro, et al. on Nov. 22, 1994. Suitable processes for ring rolling or "pre-corrugating" are described are described in U.S. Pat. No. 4,107,364 issued to Sisson on Aug. 15, 1978; U.S. Pat. No. 4,834,741 issued to Sabee on May 30, 1989; U.S. Pat. No. 5,167,897 issued to Weber, et al. Dec. 1, 1992; U.S. Pat. No. 5,156,793 issued to Buell, et al. Oct. 20, 1992; and U.S. Pat. No. 5,143,679 issued to Weber, et al. Sep. 1, 1992. The fold lines in the corrugations of a ring rolled topsheet are preferably oriented in the transverse direction so the topsheet is longitudinally extensible. In other embodiments, the fold lines could run in the longitudinal direction, both the longitudinal and transverse directions, and/or other directions. The topsheet 38 will be extensible in directions perpendicular to the fold lines.

In the particularly preferred embodiments shown in FIGS. 1–3 the topsheet 38 comprises an apertured film, such as that described in U.S. Pat. No. 4,463,045, that is provided with a strainable network so that the topsheet 38 exhibits elastic-like behavior without added elastic materials. A web material with such a strainable network may be referred to herein as a "strainable apertured web material" or, for brevity as a "strainable web material" or simply as the "web material." This type of material is also referred to herein as a structural elastic-like film or "SELF" material. A suitable strainable apertured web material is described in U.S. Pat. No. 5,518,801 issued to Chappell, et al. May 21, 1996. A portion of the topsheet 38 shown in FIG. 1 is shown as a strainable web material 60 (SELFed material). The remainder of the topsheet 38 is not shown as SELFed in order to more clearly show other features of the sanitary napkin 20.

In preferred embodiments, the topsheet 38 is rendered hydrophilic so that liquids will transfer through the topsheet 38 faster. This will diminish the likelihood that body exudates will flow off the topsheet rather than being drawn through the topsheet 38 and being absorbed by the absorbent core 42. The topsheet 38 can be rendered hydrophilic by treating it with surfactants. Suitable methods of applying surfactants are described in U.S. Pat. Nos. 4,950,254 and 5,009,653 issued to Osborn (which include incorporating the surfactant into the polymeric material of a formed film topsheet) as well as treating the surface of the component underlying the topsheet with a surfactant.

In addition, in preferred embodiments, the inner surface 38B of topsheet 38 is secured in contacting relation with an underlying absorbent layer. This contacting relationship results in liquid penetrating topsheet 38 faster. The topsheet 38 may be kept in a contacting relationship with an underlying layer by bonding the topsheet to the underlying layer. However, it is not absolutely necessary to bond the face of the topsheet 38 to the face of the underlying layer. The topsheet 38 can be maintained in contact with an underlying absorbent component, by entangling the fibers of the underlying layer with the topsheet, by fusing the topsheet 38 to an underlying absorbent layer by a plurality of discrete individual fusion bonds, or by any means known in the art.

The absorbent core 42 is positioned between the topsheet 38 and the backsheet 40. The absorbent core 42 provides the means for absorbing exudates such as menses and other body fluids. The absorbent core 42 need not have an absorbent capacity much greater than the total amount of body fluids anticipated to be absorbed. The absorbent core 42 preferably is generally compressible, conformable, and non-irritating to the user's skin.

In the embodiments shown in FIGS. 1–3, the absorbent core 42 is preferably extensible. The absorbent core 42, however, need not be extensible in all embodiments to provide a benefit. For example, a relatively inextensible core can be used in an embodiment in which the topsheet together with an underlying absorbent component (or integral absorbent component) is extensible and the topsheet and such absorbent component are not attached to the face of the core so that they are able to separate from (or "decouple" from) the core. The concept of decoupling (in general) is described in U.S. Pat. No. 5,007,906 issued to Osborn on Apr. 16, 1991. Such an embodiment is useful if the topsheet 38 is capable of extending independently of the absorbent core 42 and any other underlying components which are relatively inextensible.

The absorbent core 42 can comprise any material used in the art for such purpose including natural materials and synthetic materials. Non-limiting examples of such materials include natural materials such as comminuted wood pulp (which is generally referred to as airfelt), creped cellulose wadding, hydrogel-forming polymer gelling agents, creped tissues or creped nonwovens containing fibers comprised of absorbent or superabsorbent polymers, modified cross-linked cellulose fibers (such as those described in U.S. Pat. No. 5,217,445 issued to Young, et al. on Jun. 8, 1993), capillary channel fibers (that is, fibers having intra-fiber capillary channels such as those described in U.S. Pat. No. 5,200,248 issued to Thompson, et al. on Apr. 6, 1993), absorbent foams (such as those described in U.S. Pat. No. 5,268,224 issued to DesMarais, et al. on Dec. 7, 1993), thermally bonded airlaid materials (such as those materials described in U.S. patent application Ser. No. 08/141,156 entitled "Catamenial Absorbent Structures Having Thermally Bonded Layers for Improved Handling of Menstrual Fluids and Their Use in Catamenial Pads Having Improved Fit and Comfort" filed in the name of Richards, et al. on Oct. 21, 1993), absorbent sponges, synthetic staple fibers, polymeric fibers, peat moss, or any equivalent material or combinations of materials.

The polymeric gelling agents listed above may also be referred to as "absorbent gelling materials" ("AGM"), or "superabsorbent materials." Polymeric gelling agents are those materials which, upon contact with liquids such as water or other body liquids, imbibe such liquids and thereby form hydrogels. In this manner, liquids discharged into the absorbent core 42 can be acquired and held by the polymeric gelling agent, thereby providing the articles herein with enhanced absorbent capacity and/or improved liquid retention performance. The polymeric gelling agent which is employed in the absorbent core 42 will generally comprise particles of a substantially water-insoluble, slightly cross-linked, partially neutralized, hydrogel-forming polymer material. The polymeric gelling agent can be in many forms, including in the form of particles, flakes or fibers.

In one preferred embodiment, the absorbent core 42 is a laminate. The laminate is comprised of a layer of superabsorbent polymer material, such as in the form of particles 41, disposed between two air-laid tissues, first and second tissue layers. The first and second tissue layers provide containment of the superabsorbent polymer material, improve lateral wicking of the absorbed exudates throughout the absorbent core 42 and provide a degree of absorbency. The tissue layers can be comprised of a single tissue web which is folded with the superabsorbent material particles 41 between, or two separate sheets of the same (or different) tissue.

A suitable laminate is a superabsorbent laminate known as "WATER-LOCK" L-535 available from the Grain Processing Corporation of Muscatine, Iowa ("WATER-LOCK" registered TM by Grain Processing Corporation). Such superabsorbent laminates are disclosed in U.S. Pat. No. 4,467,012 issued to Pedersen, et at. on Aug. 21, 1984; U.S. Pat. No. 4,260,443 issue to Lindsay, et al. on Apr. 7, 1981; U.S. Pat. No. 4,578,068 issued to Kramer, et al. on Mar. 25, 1986; and U.S. Pat. No. 5,460,623 issued to Emenaker, et al. on Oct. 24, 1995.

The absorbent core materials described above can be made extensible in many different ways, including by cutting or slitting the same. FIG. 1 shows an embodiment in which the topsheet 38 is partially cut away and the absorbent core 42 is a laminate as described above which is slitted or partially slitted with transverse slits for longitudinal extensibility.

The backsheet 40 prevents the exudates absorbed and contained in the absorbent core 42 from wetting articles which contact the sanitary napkin 20 such as pants, pajamas and undergarments. The backsheet 40 should be flexible and impervious to liquids (e.g., menses and/or urine).

The backsheet 40 may comprise a woven or nonwoven material, polymeric films such as thermoplastic films of polyethylene or polypropylene, or composite materials such as a film-coated nonwoven material. Preferably, the backsheet 40 is a thin plastic film, such as a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with the pantiliner devices described herein. Another suitable backsheet material is nonwoven/film laminate described in U.S. Pat. No. 5,007,906 issued to Osborn on Apr. 16, 1991.

The backsheet 40 may have the same extensibility characteristics as the topsheet 38. The backsheet 40 can be made extensible by forming it from an elastomeric film such as the film described in U.S. Pat. No. 4,746,180 issued to Wnuk on Oct. 9, 1984. Such a film is obtained from Exxon Chemical Company of Lake Zurich, Ill. as Exxon film EXX-500 (formerly EXX-7).

Another preferred extensible backsheet 40 is an extensible adhesive film Formula #198–338 manufactured by the Findley Adhesives Company of Wauwatosa, Wis. The Findley adhesive film is a fluid impervious film capable of extending 200–300%. The Findley adhesive film is preferred because it is also elastically extensible. At least one side of this film can be used with the adhesive "as is" in the sanitary napkin 20. For example, this side of the film can be adhered to the garment-facing side 42B of the absorbent core 42. The other side of the adhesive film that forms the garment-facing side 40B of the backsheet 40 may have its adhesive surface at least partially covered (or "blocked" to eliminate its adhesive characteristics). The adhesive defining the body-facing side 40A of the backsheet can also be at least partially blocked. The exposed adhesive can be blocked in a number of suitable ways. These include, but are not limited to attaching a layer of nonadhesive material to cover the exposed adhesive, brushing or sprinkling a powdered material such as talcum power or corn starch on at least part of the exposed adhesive, and covering the exposed adhesive with a creped nonwoven material and/or nonwoven material that is oriented in a direction which allows the backsheet to extend (such as with most of its fibers running perpendicular to the desired direction of the stretch). The partial blocking of the exposed adhesive on the garment-facing side 40B of the backsheet 40 can be used with the remaining exposed adhesive to create particular adhesive patterns for fastening the backsheet to the wearer's panties.

In still other embodiments, an adhesive film can be created with one side that has an adhesive tack, and one side without tack. One suitable adhesive film having these characteristics is a composite structure comprising a nonwoven elastomeric film with a low modulus pressure sensitive adhesive, such as adhesive film Formula #198–338 which is available with a blocking film such as Formula H2031 from the Findley Adhesives Company. Such materials are further described (and used for other purposes) in U.S. Pat. No. 5,032,120 issued to Freeland, et al. on Jul. 16, 1991; and U.S. Pat. No. 5,037,416 issued to Allen, et al. on Aug. 6, 1991.

In still other embodiments, the backsheet 40 can be made extensible by performing a mechanical operation, such as pleating, corrugating, ring rolling, or SELFing the backsheet material. In the preferred embodiments shown in FIGS. 1–3 the backsheet 40 is formed by SELFing (as described in U.S. Pat. No. 5,518,801 issued to Chappell, et al. on May 21, 1996) one of the exemplary polymeric films described above. Such a SELFed backsheet material is preferred over many of the elastomeric films described above because of its relatively low cost.

The sanitary napkin 20 is also provided with one or more stiffening features 44. The stiffening features 44 may comprise any type of structure which provides a greater initial stiffness to some or all portions of the sanitary napkin 20. This greater initial stiffness is preferably present during placement of the sanitary napkin 20 into an undergarment and as the undergarment is pulled into position. The greater initial stiffness does not continue for more than a brief period of time during wear of the sanitary napkin 20. The stiffening feature 44 may comprise a separate element of the sanitary napkin 20. In other embodiments, the topsheet 38, backsheet 40, or absorbent core 42 of the sanitary napkin 20 may include the stiffening feature 44.

In a particularly preferred embodiment shown in FIGS. 1–3, the stiffening features 44 comprise a pair of brittle strip stiffening members 46 which act as brittle beams or struts. These brittle strips 46 provide the sanitary napkin 20 with a greater initial stiffness until such time as the initial stiffness threshold is exceeded during wear. The forces of the wearer sitting or walking will cause the initial stiffness threshold to be exceeded and rupture the brittle strips 46. Preferably, the brittle strips 46 will break into small fragmentary remains which may be easily contained by the topsheet 38, backsheet 40 and absorbent core 42 of the sanitary napkin 20 without significant interference with the absorbent function of the sanitary napkin 20. Rupture of the brittle strips 46 allows the sanitary napkin 20 to assume the desired generally flexible and preferably extensible state.

The brittle strip stiffening members 46 preferably extend in the longitudinal direction in a continuous fashion from the first end region 28, through the central region 32, and into the second end region 30 of the sanitary napkin 20. Preferably, the brittle strips 46 shown in FIGS. 1–2 are centered about the longitudinal centerline L of the sanitary napkin 20 and are disposed between the backsheet 40 and the absorbent core 42. The strips 46 may less preferably be disposed between the topsheet 38 and the absorbent core 42. In an even less preferred embodiment, the brittle strips 46 may be attached to the garment facing side of the backsheet 40B. In this case, the topsheet 38, backsheet 40 and absorbent core 42, will not cooperate to contain the fragments of the strips 46 after the strips have ruptured.

The brittle strip stiffening members 46 may comprise any suitable material that has the desired characteristics. For example, the brittle strip stiffening members 46 may comprise strips of woven or nonwoven material which have been rendered stiff and brittle through the application of spray starch. Strips of plaster bandages which have been allowed to dry have also been found to work well as brittle strip stiffening members 46.

Figure 7:
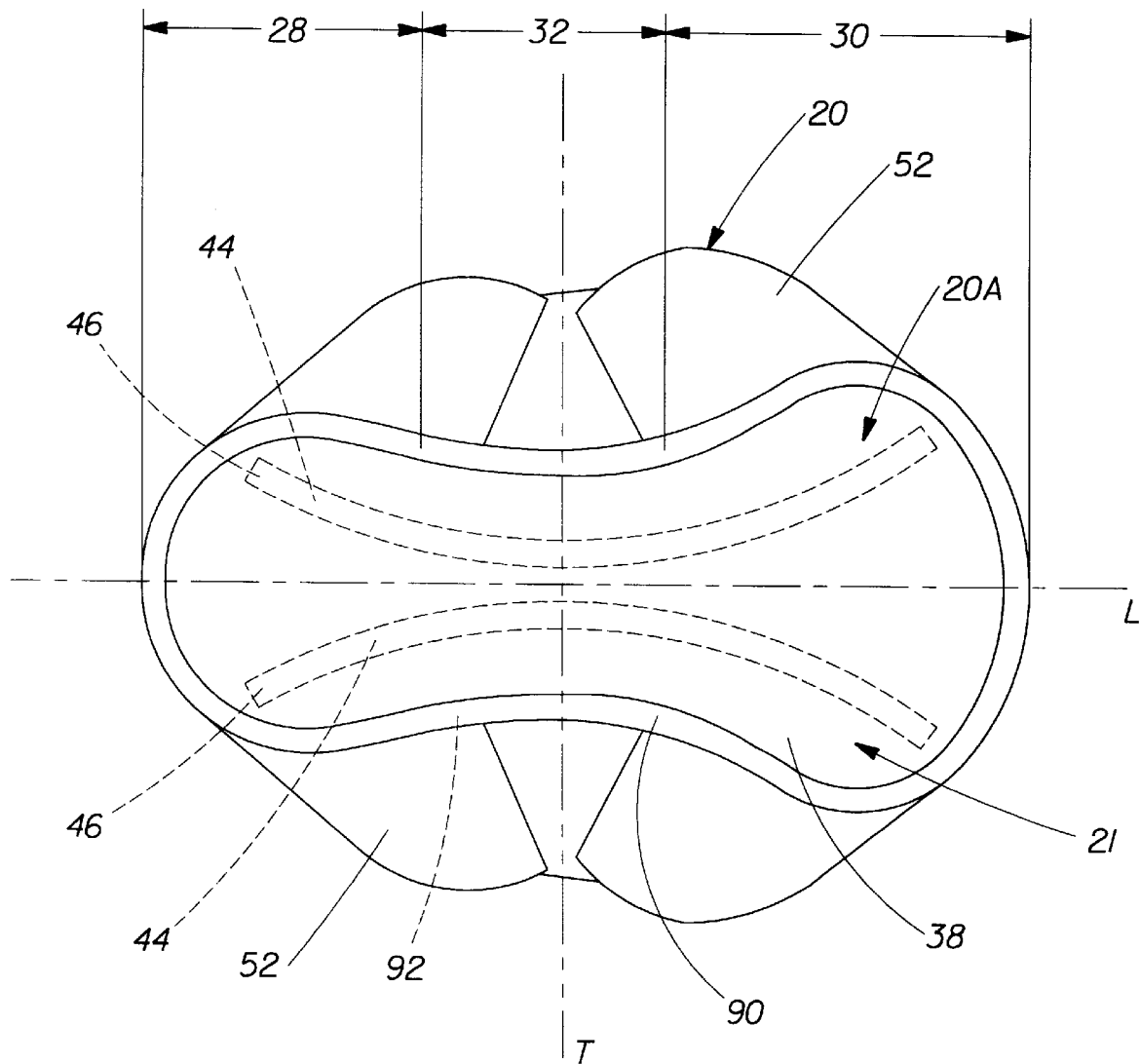
FIG. 7 is a simplified top plan view of an alternative preferred embodiment of the sanitary napkin of the present invention.

Several variations on the brittle strip stiffening members 46 are also possible. For example, FIG. 7 shows a sanitary napkin in which the stiffening features 44 comprise a pair of brittle strips 46 which are generally curved rather than straight. Preferably in this embodiment the brittle strips 46 are oriented symmetrically about the longitudinal centerline as shown in FIG. 7, but such an arrangement is not necessary. The brittle strip stiffening members 46 shown in FIG. 7 may be constructed of strips of material stiffened by spray starch or strips of plaster bandage which have been allowed to dry. Any other construction which creates a brittle beam or strut and will impart an initial stiffness to the sanitary napkin 20 until the initial stiffness threshold is exceeded may also be used.

Figure 12:
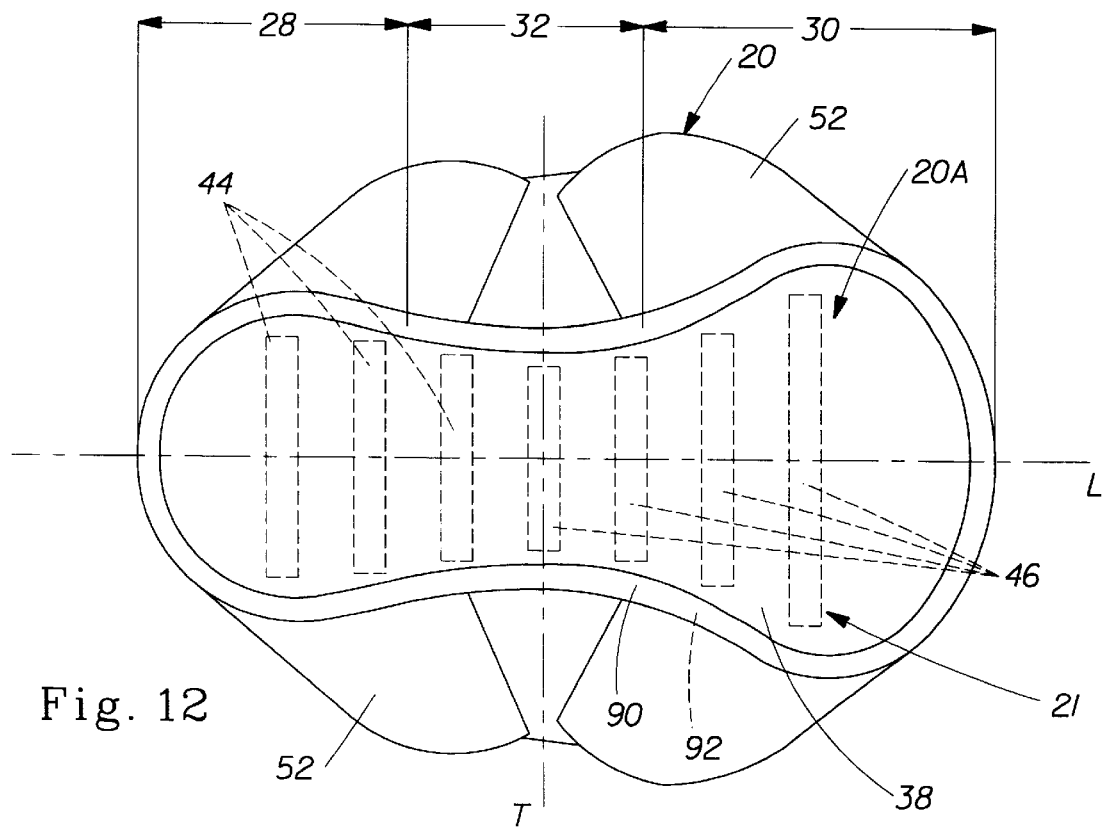
FIG. 12 is a simplified top plan view of an alternate embodiment of the sanitary napkin of the present invention.

Additional variations with brittle strip stiffening members 46 include absorbent articles with a single brittle strip 46 as shown in FIG. 8. In a less preferred embodiment, the brittle strips 46 may be oriented in the transverse direction as shown in FIG. 12. A variety of variations are possible as any number of brittle strip stiffening members 46 may be used. In these or other embodiments, the brittle strips 46 may vary in length and be oriented in different directions.

Figure 5:
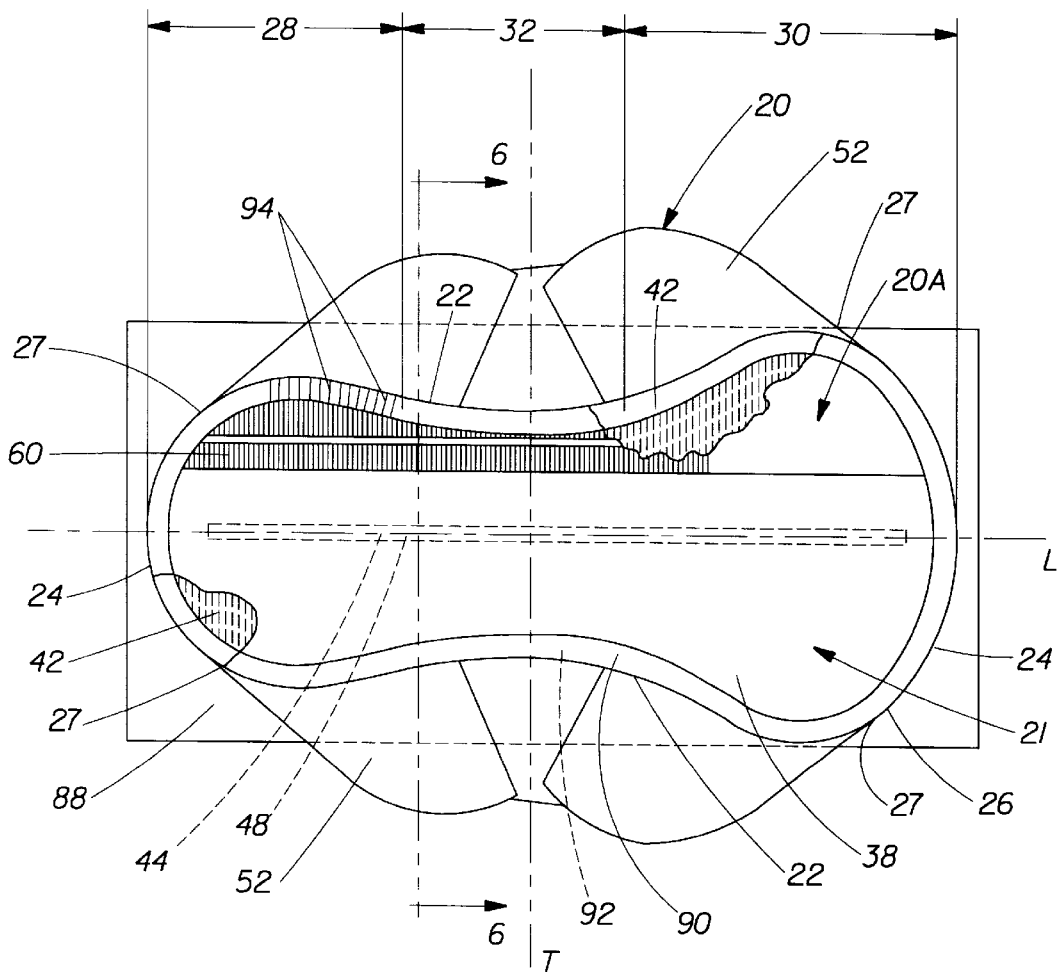
FIG. 5 is a top plan view of an alternate preferred embodiment of sanitary napkin of the present invention.
Figure 6:
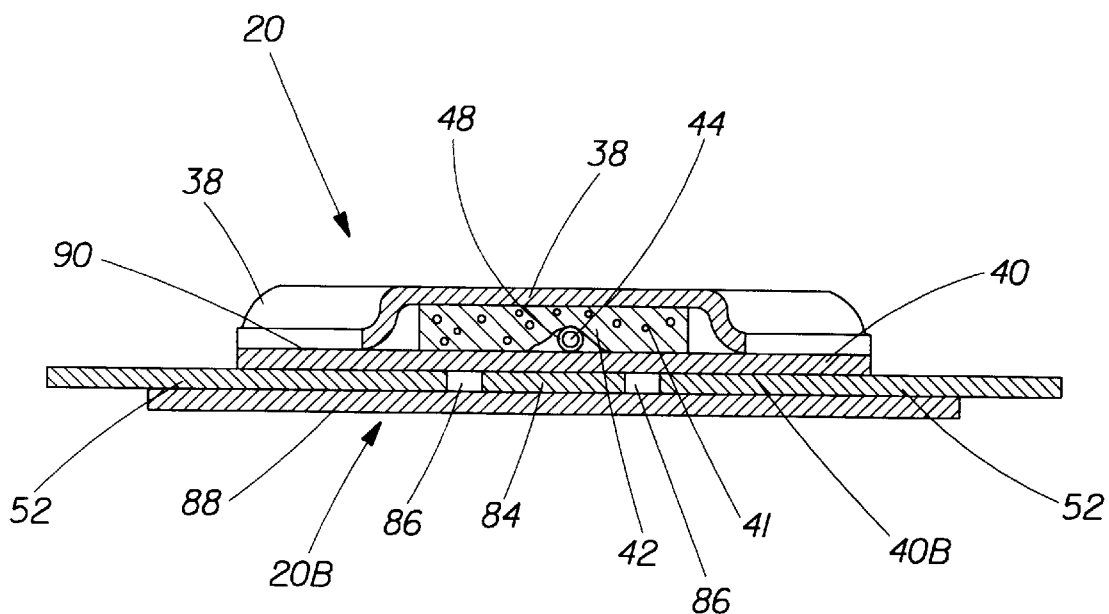
FIG. 6 is a sectional view taken along line 6—6 of the sanitary napkin shown in FIG. 5.

In an alternate particularly preferred embodiment shown in FIGS. 5–6, the stiffening feature 44 may comprise a separate tube shaped element constructed from a tissue or nonwoven layer wrapped in a polypropylene layer or from a prolyproylene layer wrapped in a tissue or nonwoven layer. The polypropylene layer is melted into the tissue or nonwoven layer thereby creating a relatively stiff tube structure 48. This relatively stiff tube structure 48 acts as the stiffening feature 44 in the preferred embodiment shown in FIGS. 5–6. One polypropylene material which works well for this purpose is known as "CELESTRA" which is available from Fiberweb, North America of Simpsonville, S.C. A suitable nonwoven layer is obtained as "DANWEB" material #1079–2338 and 2339 from Dan Web of Aarhus, Denmark.

The tube structure stiffening member 48 preferably extends along the longitudinal centerline from the first end region 28, through the central region 32, and into the second end region 30 of the sanitary napkin 20. The tube structure stiffening member 48 may have any suitable cross section. Preferably, the tube structure 48 is disposed between the absorbent core 42 and the backsheet 40 of the sanitary napkin. When the initial stiffness threshold of the sanitary napkin 20 is exceeded (e.g., from the wearer sitting down) the tube structure stiffening member 48 collapses and ceases to provide a greater stiffness to the sanitary napkin 20. Once collapsed, the tube shaped stiffening member 48 preferably does not return to its tube shape and offers little resistance to bending, thus allowing the sanitary napkin 20 to exhibit its generally flexible and extensible characteristics.

Figure 6A:
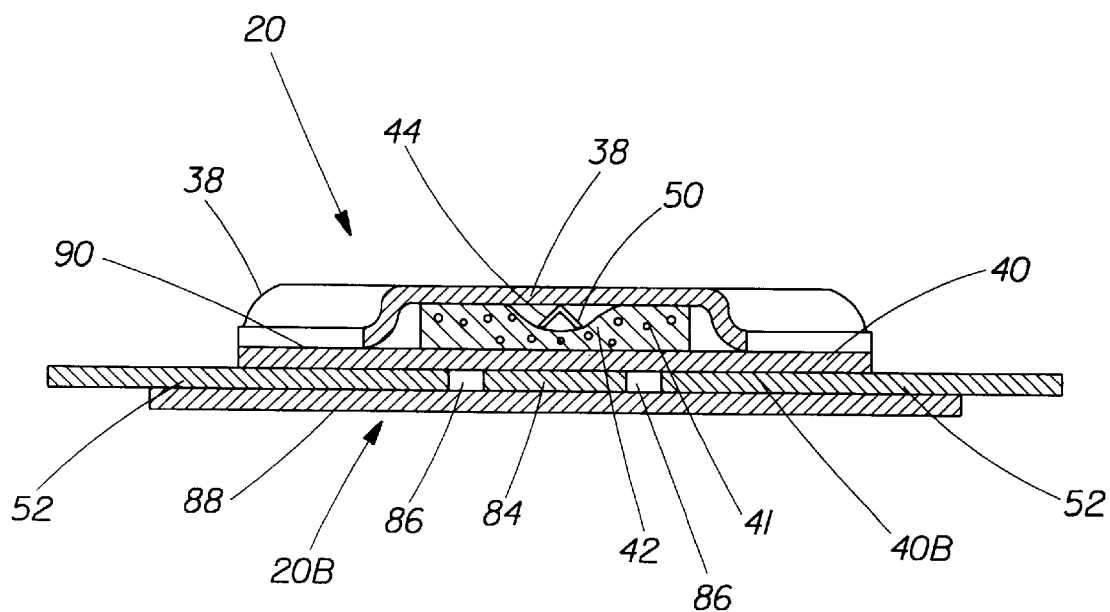
FIG. 6A is a sectional view similar to FIG. 6 but showing a variation on the preferred embodiment shown in FIG. 6.

In a variation of this embodiment, the polypropylene layer is melted into a tissue layer both of which are in the shape of an inverted "V" as shown in FIG. 6A. This creates an initially stiff inverted "V" 50 which functions as the stiffening feature 44 of the sanitary napkin 20 shown in FIG. 6A. As with the tube shaped stiffening member 48, the initially stiff inverted "V" 50 offers resistance to bending by virtue of its shape. The initially stiff inverted "V" 50 structure also collapses when the initial stiffness threshold of the sanitary napkin 20 is exceeded. Subsequent to such collapse, the initially stiff inverted "V" 50 offers little resistance to bending, thus allowing the sanitary napkin 20 to exhibit its generally flexible and extensible characteristics.

Additional variations on this embodiment are also possible. The stiffening feature(s) 44 may comprise any structure which offers resistance to bending by virtue of its shape. The structure should be constructed in such a manner that it will collapse or otherwise deform when subjected to the forces of wear, thus losing the shape which provided the described bending resistance. During wear, the structure preferably should not continue to impart stiffness or bending resistance to the absorbent article described above.

The sanitary napkin 20 may contain any number of tube shaped 48, inverted —V" shaped 50, or other shaped stiffening members 44 in a variety of lengths. These stiffening members 44 may be oriented in any direction.

Figure 10:
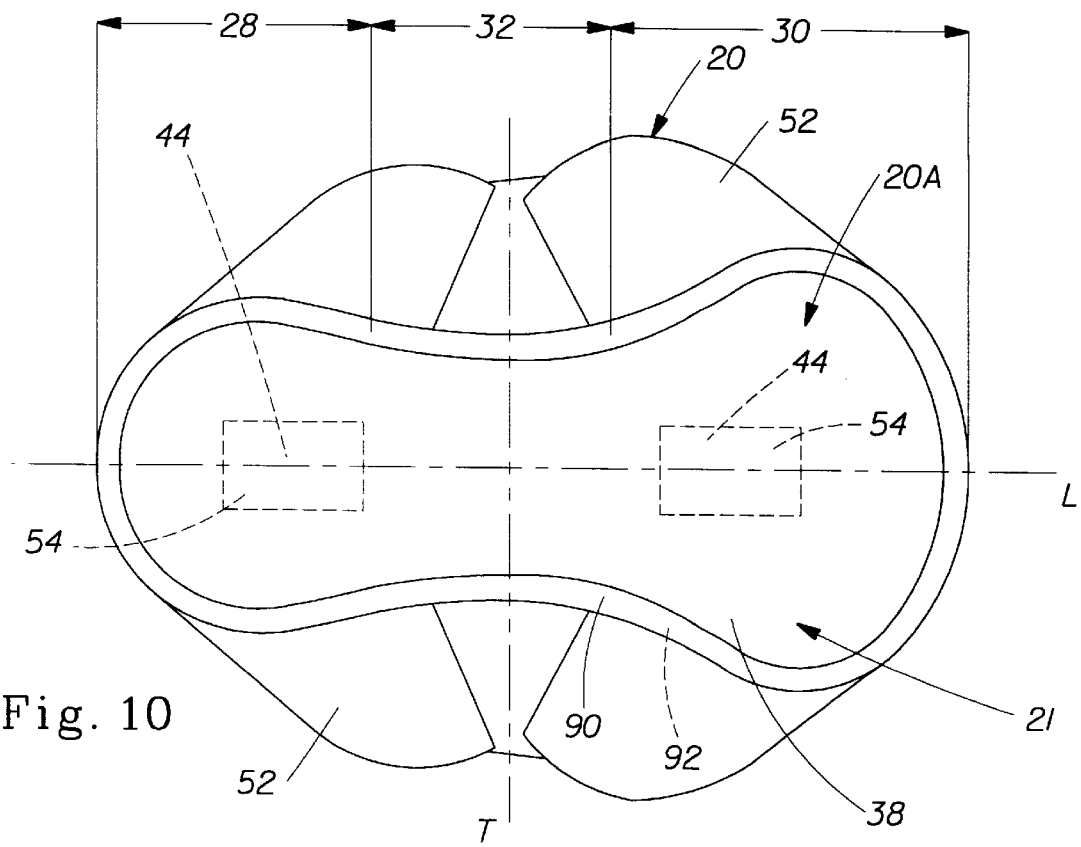
FIG. 10 is a simplified top plan view of a variation of the embodiment shown in FIG. 9.
Figure 11:
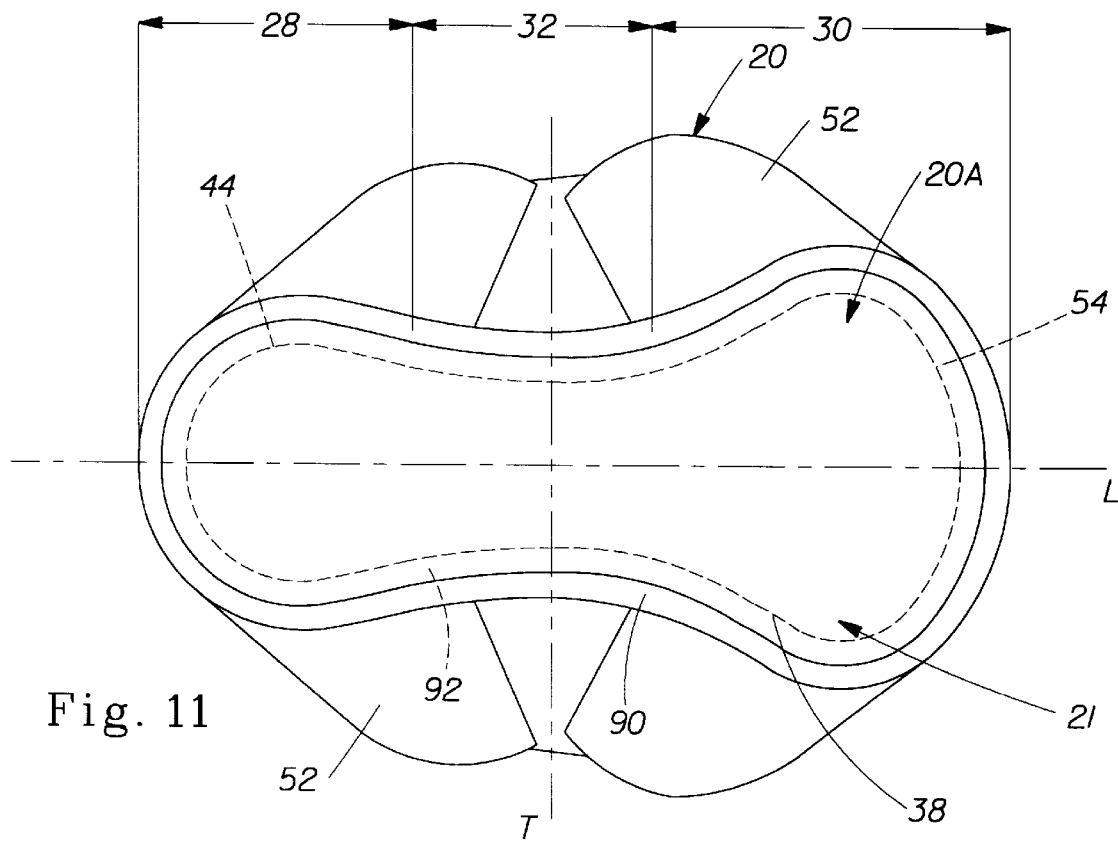
FIG. 11 is a simplified top plan view of an additional embodiment of the sanitary napkin of the present invention.

In an additional series of preferred embodiments shown in FIGS. 9–11, the stiffening features 44 comprise zones of stiffness 54 rather than beams or struts. The zones of stiffness 54 can comprise an integral part of one of the elements of the absorbent article, preferably the absorbent core 42, or less preferably the topsheet 38 or backsheet 40. Alternatively, the zones of stiffness 54 may comprise a separate element preferably positioned above the absorbent core 42, below the absorbent core 42, or within the absorbent core 42 (e.g. such as between layers of a laminate absorbent core).

In one preferred embodiment, the sanitary napkin 20 shown in FIG. 9 has three zones of stiffness 54. Two zones of stiffness 54 are located generally in the second end region 30 while the third is located generally in the first end region 28 and may extend into the central region 32. Preferably, the zones of stiffness are located symmetrically about the longitudinal centerline L. In another preferred embodiment shown in FIG. 10, sanitary napkin 20 is provided with two zones of stiffness 54. FIG. 11 shows a sanitary napkin 20 provided with a zone of stiffness 54 around the perimeter of the sanitary napkin 20 inboard of the seam 90. These examples are representative and the precise arrangement of the zones of stiffness 54 may differ. Any number of zones 54 may be used and the size, shape, and orientation of each may be varied so as to provide the absorbent article with an initial stiffness threshold meeting the objects of the invention described above.

The zones of stiffness 54 may comprise a polypropylene nonwoven material such as "CELESTRA" nonwoven material melted into a tissue layer such as "DANWEB" tissue layer. The resulting composite serves as the stiffening feature 44 and is bonded to the top or bottom of the absorbent core 42 in a suitable manner known in the art. In variations on this embodiment, any material from which a brittle film may be formed may be used for the zones of stiffness 54. For example, a thin film of sodium silicate, known as water glass, may serve as a suitable material from which to construct the zones of stiffness 54. Pieces of tissue or nonwoven material stiffened with plaster, cornstarch, or other material which results in a brittle film may also be used to construct zones of stiffness 54. The resulting stiffened tissue or nonwoven material is bonded to the top or bottom of the absorbent core 42 as described above in a manner known in the art.

The zones of stiffness 54 may also be created as an integral part of the absorbent core 42, less preferably the backsheet 40, or even less preferably the topsheet 38. Such integral zones of stiffness 54 in a preferred embodiment may be created by stiffening the garment facing side of the absorbent core 42B with a thin layer of sodium silicate (water glass). Alternatively, a thin layer of plaster or other suitable material may be used for this purpose. In a less preferred embodiment, the body facing side of the absorbent core 42 may be stiffened in any manner described above. Similarly, in even less preferred embodiments, the backsheet 40 or the topsheet 38 may be provided with an integral zone of stiffness 54 using any of the materials previously described or another suitable material.

The components of the main body portion described above (topsheet 38, backsheet 40, absorbent core 42, and stiffening member 44) can be assembled in any suitable manner. In the preferred embodiment shown in FIGS. 1–3, the components of the main body portion are assembled in a "sandwich" configuration with the components sized so that the edges of the topsheet 38 and backsheet 40 extend outward beyond the edges of the absorbent core 42. The topsheet 38 and backsheet 40 are preferably at least partially peripherally joined using known techniques. As shown in FIG. 1, the topsheet 38 is preferably secured to backsheet 40 along a seam, such as seam 90. Seam 90 is preferably liquid impervious. The seam 90 can be formed by any means commonly used in the art for this purpose such as by gluing, crimping, or heat-sealing.

The term "joined," as used herein, encompasses configurations in which an element is directly secured to another element by affixing the element directly to the other element; configurations in which the element in indirectly secured to the other element by affixing the element to intermediate member(s) which in turn are affixed to the other element; and configurations in which one element is integral with the another element, i.e., one element is essentially part of the other element.

The components of the sanitary napkin 20 can be joined together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one components onto another components, extruding one components onto another, or by any other means known in the art. Suitable means for attaching the components of the sanitary napkin are described in U.S. patent application Ser. No. 07/810,774 filed in the name of Cree, et al. on Dec. 17, 1991 (PCT Patent Publication No. WO 93/11725 published on Jun. 24, 1993).

When the main body portion is comprised of extensible components, the components can be joined together in any suitable manner than allows the main body portion to extend. The combining of the topsheet 38 and backsheet 40 in an extensible product cannot always be accomplished by traditional sealing methods or materials used for nonstretchable products. Bonds formed by traditional heat and pressure methods often do not stretch or are embrittled so that they easily rip or tear when the product is stretched. This is particularly a problem when the topsheet 38 and the backsheet 40 have different elastic properties, or melting points, or are sufficiently different in composition that sealing is difficult even when these components do not stretch.

In a particularly preferred extensible sanitary napkin 20 embodiment shown in FIGS. 1–3, the portions of the topsheet 38 and backsheet 40 at the edges of the topsheet 38 and backsheet 40 are secured together using an extensible adhesive 92 around the perimeter 26 of the sanitary napkin and in addition, a preferred distribution of mechanical bonds 94 in the perimeter area 26. The extensible adhesive 92 provides an impervious extensible seal around the perimeter 26 of the sanitary napkin 20. The mechanical bonds 94 (only a portion of which are shown if FIG. 1) provide added strength. The mechanical bonds 94 are arranged in intermittent zones (or regions) of bonded and nonbonded areas.

The sanitary napkin 20 preferably also comprises side wrapping elements 52 located along each longitudinal side edge 22 of the main body portion 21. Such side wrapping elements are described in U.S. application Ser. No. 08/192, 240 filed in the name of Osborn III et al. on Feb. 4, 1994 (PCT Application Publication No. WO 95/20931 published Aug. 10, 1995).

The garment surface 20B of the sanitary napkin 20 and the garment surface of the side wrapping elements 52 may include fasteners for attaching the sanitary napkin 20 the undergarment of the wearer.

FIG. 3 shows that in the particularly preferred embodiment shown in the drawings, the sanitary napkin is provided with two end fasteners 84 and perimeter fastener 86, a fastener that is disposed around the perimeter of the main body portion 21, which are adapted to secure the portion of the sanitary napkin 20 underlying the main body portion 21 to the crotch region of an undergarment. The end fasteners 84 are preferably inextensible fasteners, such as inextensible adhesive patches. The end fasteners 84 serve to firmly anchor the ends of the main body portion 21 in the wear's panties. The perimeter fastener 86 is preferably an extensible fastener, such as an extensible adhesive. The extensibility of the perimeter fastener 86 assists the portions of the sanitary napkin between the ends of the main body portion 21 in extending during use.

The inextensible end fasteners 84 can comprise any adhesive or glue used in the art for such purposes with pressure-sensitive adhesives being preferred. Suitable adhesives are Century A-305-IV manufactured by the Century Adhesives Corporation, Instant Lock 34-2823 manufactured by the National Starch Company, 3 Sigma 3153 manufactured by 3 Sigma, and Fuller H-2238ZP manufactured by the H. B. Fuller Co. Suitable adhesive fasteners are also described in U.S. Pat. No. 4,917,697.

Suitable extensible adhesives for use as the perimeter fastener 86 include extensible adhesives, per se, and extensible adhesive/backsheet combinations. Any extensible adhesives known in the art can be used. Suitable extensible adhesive/backsheet combinations include, but are not limited to non-extensible adhesive used on an extensible backsheet material such as 3 Sigma 2474 available from Anchor Continental, Inc., 3 Sigma Division, of Covington, Ohio; elastically stretchable adhesive films such as Findley adhesive 198–338, or an elastically stretchable adhesive film known as 3M XPO-0-014 available from the Minnesota Mining and Manufacturing Company of St. Paul, Minn.; or spray adhesives such as 3M adhesive 1442 on a low modulus elastic film. The end fasteners 84 and perimeter fasteners 86 are preferably releasably covered prior to use of the sanitary napkin 20 by release paper 88 shown in FIG. 1.

When the sanitary napkin of the present invention is removed from its packaging, the stiffening feature maintains the sanitary napkin in an initially stiffened condition. The center of the main body portion is placed in the crotch portion of the wearer's panty with the backsheet in contact with the inner surface of the crotch portion of the panty and one end of the main body portion extending towards the front section of the panty and the other end towards the back section. The end fasteners and perimeter adhesive combine to maintain the main body portion in position. The distal portions of the side wrapping elements are folded around the elasticized edges of the panty. The side wrapping elements may be secured to the underside of the panty with a flap adhesive, but such a flap adhesive is not necessary. Once the sanitary napkin is secured to the panty in position as described, the wearer pulls up the panty achieving body contact with the sanitary napkin. The forces exerted on the sanitary napkin by the wearer's body will cause the stiffening feature to cease to provide the increased initial stiffness allowing the sanitary napkin to assume a more flexible condition.

The terms "panty liner" and "pantiliner" refer to absorbent articles that are less bulky than sanitary napkins which are generally worn by women between their menstrual periods. Suitable absorbent articles in the form of pantiliners that could be provided with the stiffening feature described herein are disclosed in U.S. Pat. No. 4,738,676 entitled "Pantiliner" issued to Osborn on Apr, 19, 1988.

The term "incontinence article" refers to pads, undergarments (pads held in place by a suspension system of some type, such as a belt, or the like), inserts for absorbent articles, capacity boosters for absorbent articles, briefs, bed pads, and the like, regardless of whether they are worn by adults or other incontinent persons. Suitable incontinent articles that can be provided with the stiffening feature described herein are disclosed in U.S. Pat. No. 5,304,161 issued to Noel, et al. on Apr. 19, 1994; and U.S. Pat. No. 5,300,054 issued to Feist, et al. on Apr. 5, 1994.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article comprising a liquid pervious topsheet, a liquid impervious backsheet joined to said topsheet, and an absorbent core positioned between said topsheet and said backsheet, wherein said absorbent article has a first condition, and a second condition, said first condition being an initially stiffened condition, said second condition being a more flexible condition, and wherein said absorbent article transitions from said first condition to said second condition after being subjected to forces exceeding a pre-determined initial stiffness threshold.

2. An absorbent article for wearing in an undergarment, said absorbent article comprising:
    a liquid pervious topsheet;
    a liquid impervious backsheet joined to said topsheet; and
    an absorbent core positioned between said topsheet and said backsheet; wherein at least one of said topsheet, said backsheet, and absorbent core serves as a stiffening feature, said stiffening feature being capable of maintaining at least portions of said absorbent article in an initially stiffened condition when said absorbent article is handled prior to wear and placed in said undergarment, said stiffening feature becoming more flexible when said absorbent article is worn so that said stiffening feature ceases to maintain said portions of said absorbent article in said initially stiffened condition, allowing said absorbent article to assume a more flexible condition.

3. The absorbent article of claim 2 wherein said stiffening feature comprises at least one zone of stiffness.

4. The absorbent article of claim 3, said absorbent article having a perimeter, wherein said topsheet and said backsheet are joined at said perimeter to form a perimeter seam and wherein one of said at least one zone of stiffness is a perimeter zone of stiffness located inboard of said perimeter seam.

5. The absorbent article of claim 2 wherein said stiffening feature is said topsheet.

6. The absorbent article of claim 5 wherein said stiffening feature is formed by stiffening said topsheet with cornstarch.

7. The absorbent article of claim 2 wherein said stiffening feature is said backsheet.

8. The absorbent article of claim 7 wherein said stiffening feature is formed by stiffening said backsheet with cornstarch.

9. The absorbent article of claim 2 wherein said stiffening feature is said absorbent core.

10. The absorbent article of claim 9 wherein said stiffening feature is formed by stiffening said absorbent core with cornstarch.

11. The absorbent article of claim 9 wherein said stiffening feature is formed by applying a film to at least one side of said absorbent core.

12. An absorbent article for wearing in an undergarment said absorbent article having a garment facing side and a body facing side, said absorbent article further comprising:
    a liquid pervious topsheet;
    a liquid impervious backsheet joined to said topsheet;
    an absorbent core positioned between said topsheet and said backsheet; and
    at least one stiffening member juxtaposed at least one of said topsheet, said backsheet, and said absorbent core, wherein said stiffening member maintains at least portions of said absorbent article in an initially stiffened condition when said absorbent article is handled prior to wear and placed in said undergarment, and wherein as a consequence of mechanical forces exerted on said absorbent article by a wearer's body, said stiffening member ceases to maintain said portions of said absorbent article in said initially stiffened condition when said absorbent article is worn, allowing said absorbent article to assume a more flexible condition.

13. The absorbent article of claim 12 wherein said stiffening member comprises at least one brittle strip that breaks into a plurality of pieces when said absorbent article is worn.

14. The absorbent article of claim 13 wherein said brittle strip is disposed between said topsheet and said backsheet.

15. The absorbent article of claim 14 wherein said brittle strip is disposed between said backsheet and said absorbent core.

16. The absorbent article of claim 14 wherein said brittle strip is disposed between said topsheet and said absorbent core.

17. The absorbent article of claim 14 wherein said brittle strip comprises a strip of plaster material.

18. The absorbent article of claim 14 wherein said brittle strip a comprises a strip of material which has been stiffened by corn starch.

19. The absorbent article of claim 12 wherein said stiffening member comprises a tube-shaped structure.

20. The absorbent article of claim 19 wherein said tube-shaped structure is constructed by melting a polypropylene material onto a tissue layer.

21. The absorbent article of claim 12 wherein said stiffening member comprises an inverted-"V" shaped structure.

22. The absorbent article of claim 21 wherein said inverted-"V" shaped structure is constructed by melting a polypropylene material onto a tissue layer.

23. The absorbent article of claim 12 wherein said stiffening member ceases to maintain said portions of said absorbent article in said initially stiffened condition as a consequence of the mechanical forces exerted on said absorbent article by the wearer's body in the absence of moisture.

* * * * *